United States Patent [19]

Andrews

[11] Patent Number: 5,063,249

[45] Date of Patent: Nov. 5, 1991

[54] NONIRRITATING TEAT DIP AND METHOD

[75] Inventor: Jeffrey F. Andrews, Stillwater, Minn.

[73] Assignee: Minnesota Mining and Manufacturing Company, St. Paul, Minn.

[21] Appl. No.: 426,501

[22] Filed: Oct. 23, 1989

Related U.S. Application Data

[63] Continuation of Ser. No. 878,573, Jun. 25, 1986, abandoned, which is a continuation-in-part of Ser. No. 760,241, Jul. 29, 1985, abandoned.

[51] Int. Cl.$^5$ .............................................. A61K 31/13
[52] U.S. Cl. ..................................... 514/673; 514/564
[58] Field of Search ......................................... 514/673

[56] References Cited

U.S. PATENT DOCUMENTS

| | | | |
|---|---|---|---|
| 2,246,526 | 6/1941 | Kyrides | 514/673 |
| 2,739,922 | 3/1956 | Shelanski | 167/70 |
| 3,993,777 | 11/1976 | Caughman et al. | 424/329 |
| 4,025,628 | 5/1977 | Dewey et al. | 424/249 |
| 4,199,564 | 4/1980 | Silver et al. | 424/80 |
| 4,434,181 | 2/1984 | Narjsm et al. | 424/326 |

OTHER PUBLICATIONS

Dairy Science Abstract of Teofanovic, M., Veferinarski Glasnik, vol. 28, 1974, pp. 781–786.
M. S. Balsam et al., "Cosmetics Science and Technology", 1979, pp. 34, 35, 81, 82 and 101.
Report No. R-2846 (dated Mar. 1969) provided by Th. Goldschmidt A. G.
M. Sipka, Arch. Lebensmittelhygiene, 1972, 23(8) (together with non-certified English translation).
Chemical Abstracts 68 (1968), #43156b.
Chemical Abstracts 92 (1980), #11239k.

*Primary Examiner*—James H. Reamer
*Attorney, Agent, or Firm*—Gary L. Griswold; Walter N. Kirn; Philip M. Goldman

[57] ABSTRACT

A nonirritating germicidal animal test dip comprising certain dodecylaminolkylamine derivatives, an emollient and a film-forming ingredient. A method for controlling mastitis in dairy cows is also described.

19 Claims, No Drawings

NONIRRITATING TEAT DIP AND METHOD

CROSS-REFERENCE TO RELATED APPLICATION

This is a continuation of application Ser. No. 06/878,573 filed June 25, 1986, now abandoned, which is a continuation-in-part of my copending application U.S. Ser. No. 760,241, filed July 29, 1985 now abandoned.

Technical Field

This invention relates to a novel teat dip comprising a germicidal agent. This invention also relates to a method for controlling mastitis in dairy cows using such a teat dip.

BACKGROUND OF THE INVENTION

The formulation of a teat dip is a complex process which requires that numerous ingredients be compatible and provide an effective product. Barrier-type teat dips and germicidal teat dips and combinations of the two are the main types of dips known. In practice, a teat is dipped into a teat dip subsequent to milking and the resulting film is allowed to remain on the teat until the next milking which is generally 8 to 12 hours later.

Although many germicides have been tried in teat dips, it is very difficult to find germicides which are satisfactory. A satisfactory germicide must be sufficiently effective in killing various microbes, provide a stable dip formulation, be nonirritating to the teat for the period during which it remains on the teat, and be relatively economical, since it is the major active ingredient in the formulation.

Some of the prior art germicides described as useful in teat dips include chlorinated cyanurates (U.S. Pat. No. 4,025,628), chlorhexidine (U.S. Pat. No. 4,434,181), alkyl quaternary ammonium salts (U.S. Pat. No. 3,993,777), iodine (U.S. Pat. No. 2,739,922) and combinations of nitroalkanols and aminocarboxylic acids (U.S. Pat. No. 4,199,602).

"Tego 51" and "Tego 51B" are germicidal products available from Th. Goldschmidt A.G. (Essen, West Germany). These products are complex mixtures of a variety of alkylamines and N-substituted glycines. Analysis conducted on behalf of the inventor has indicated that the major germicidal components present are 3-(n-dodecylamino)-propylamine and 2-[2-(n-dodecylamino)ethylamino]ethylamine.

A standard primary skin irritation test on rabbits (Draize test) run on "Tego 51" containing 9% "active ingredients" showed the product to be severly corrosive to skin. A severe erythema with eschar formation and severe edema was followed within seven (7) days by complete necrosis of the skin at the test site. Even when diluted to 1.0% and 0.5% concentrations, the "Tego 51" showed moderate to severe erythema and edema after 24 hours. Moderate necrosis was also seen at these concentrations. The above data are included in Report No. R-2846 (dated March 1969) provided by Th. Goldschmidt A. G., the manufacturer of "Tego 51".

M. Sipka, Arch. Lebensmittelhygiene, 1972, 23(8), 176-9 discloses the use of "Tego 51/15 DL" as an udder wash. Similarly, vendor literature provided by Th. Goldschmidt A. G. discloses the use of "Tego 51" as an udder wash. Use of a product as an udder wash involves contact of the product with the teat for only a short period of time on the order of seconds or at most a minute or two just prior to milking.

Germicides as obviously irritating as "Tego 51" and "Tego 51B" would not usually be considered suitable for use in a teat dip which entails prolonged contact of the germicide with the teat, even though their potency, spectrum of activity and cost make them otherwise very attractive candidates. Even more unlikely would be their use in a concentrated teat dip because of the chance of severe injury to the cow if the product was accidentally used undiluted. Surprisingly, however, a way to use these potent germicides in a teat dip suitable for daily use has been found.

SUMMARY OF THE INVENTION

The present invention relates to improved animal teat dip formulations. In particular, it relates to novel teat dips which are effective and yet nonirritating even when applied as a concentrate. The invention also relates to a method of using the formulations.

The teat dips of the present invention are formulations comprising, as a homogeneous mixture, i) 3-(n-dodecylamino)propylamine and/or 2-[2-(n-dodecylamino)-ethylamino]ethylamine, either or both present as the free base or as a pharmaceutically acceptable acid addition salt; ii) an emollient; and iii) a film forming ingredient. Optionally (and preferably) the formulations further include a dye, preferably a dye generally recognized as safe, and/or an antifoaming agent. Teat dip concentrates are also described.

The formulations of the present invention are provided as concentrates to be diluted with water or as solutions ready to be used on the teats of a cow. Teat dips are ordinarily used and provided as dilute solutions. It is somewhat easier to formulate many of the known dips as dilute mixtures since dilute mixtures are generally more stable than concentrated mixtures. On the other hand, concentrates are much less expensive to provide and to ship. Although concentrates are more difficult to formulate, this invention provides concentrated formulations with excellent stability and properties. In fact, the preferred concentrates of the invention are generally more stable than the corresponding diluted formulations.

It was surprising to find that this invention provided nonirritating concentrated formulations in view of the knows skin irritancy of "Tego 51" and "Tego 51B".

DETAILED DESCRIPTION OF THE INVENTION

The present invention relates to teat dip concentrates and dilute formulations for use in providing germicidal protection to the teats of dairy cows.

As used in the instant specification and claims, "substantially stable" as used in connection with "homogeneous mixture" denotes a homogeneous mixture which remains homogeneous for a period of at least about ninety (90) days at room temperature. By "substantially nonirritating" is meant that teats dipped with teat dip twice daily for twenty one (21) consecutive days show no substantial irritation. By "pharmaceutically acceptable acid addition salt" is meant any salt which exhibits suitable germicidal activity and is not substantially less safe than the free base.

The 3-(n-dodecylamino)propylamine and 2-[2-(n-dodecylamino)ethylamino]ethylamine useful as the germicides in the formulations of the present invention are available commercially in "Tego 51" and "Tego 51B" from Th. Goldschmidt Co., Essen, West Germany.

Both "Tego 51" and "Tego 51B" are aqueous solutions which comprise 3-(n-dodecylamino)propylamine and 2-[2-(n-dodecylamino)ethylamino]ethylamine as the principal germicidal components. It is believed that the principal components are present in "Tego 51" and "Tego 51B" as the hydrochloride salts. Also present in a significant amount is $CH_3(CH_2)_{11}NHCH_2CH_2CH_2NHCH_2COOH$, which may be named N-[3-(n-dodecylamino)propyl]glycine and which too is believed to be present as the hydrochloride salt. The latter compound, however, has been found to be much less active than the former two against *Staphylococcus aureus* and *Escherichia coli*. Numerous other components are also present in "Tego 51" and "Tego 51B", but the germicidal activity exhibited by the above "Tego" products is believed to be attributable primarily to those components mentioned above (particularly the first two mentioned).

The teat dip concentrates of the present invention comprise 3-(n-dodecylamino)propylamine, 2-[2-(n-dodecylamino)ethylamine]ethylamine, and/or pharmaceutically acceptable acid-addition salts of one or both of the foregoing in a total amount of about 0.25 to 2.5% based on the total weight of the concentrate. All ranges of amounts indicated in the instant specification and claims for the germicidal component(s) are amounts by weight based on the free base whether or not the free base or a pharmaceutically acceptable salt thereof is employed.

Preferably, the teat dip concentrate of the present invention comprises 3-(n-dodecylamino)propylamine or the hydrochloride salt thereof in an amount of about 0.2 to 1.8% by weight, and more preferably about 0.4 to 0.9% based on the total weight of the concentrate, and further comprises 2-[2-(n-dodecylamino)ethylamino]ethylamine or the hydrochloride salt thereof in an amount of about 0.05 to 0.7% by weight and more preferably 0.09 to 0.4% based on the total weight of the concentrate.

An ingredient that is preferably used in many commercial teat dips, and is present in the teat dips of the present invention, is an emollient. Most germicides are at least mildly irritating to skin and an ingredient to counteract any potential irritation is essential. It is well known to researchers and dairymen that irritated teats are more prone to mastitis infection than are soft, healthy teats. Several emollient, anti-irritant, or moisturizing type ingredients were evaluated. Water soluble, acetylated polyethoxylated lanolin derivatives such as Amerchol's "Solulan 97" and "Solulan 98" were tried unsuccessfully since a stable homogeneous mixture did not result. These gave cloudy solutions which separated and gelled after only 2 days aging. Glycerine was tried but was also incompatible with the germicide ("Tego 51B") since a stable homogeneous mixture did not result. A ring of gelled material formed at the top of the solution when these two were combined. The same phenomenon occurred when propylene glycol was tested as an emollient with "Tego 51B" germicide.

Suitable emollients are the polyethylene glycol methyl glucosides such as "Glucamate DOE 120" (a polyethoxylated glucose dioleate containing 120 ethoxy units in the polyethylene glycol moiety, available from Amerchol Corporation, Edison, N. J.); "Glucam E10" (a polyethoxylated methyl glucose containing 10 ethoxy units from Amerchol Corporation); "Glucam E-20" (a polyethoxylated methyl glucose containing 20 ethoxy units in the polyethylene glycol moiety, available from Amerchol Corporation; "Glucam P-10" (a polypropoxylated methyl glucose containing 10 propoxy units in the polyethyleneglycol moiety, available from Amerchol Corporation); and "Glucam P-20" (a polypropoxylated methyl glucose containing 20 propoxy units in the polyethyleneglycol moiety, available from Amerchol Corporation). These emollients provide formulations which would be found to be stable over a range of temperatures from 0° to 50° C. It is also believed that other polyethoxylated glucosides would also be suitable. Other emollients which are suitable are hydrogenated starch hydrolysates available from the trade designations "Hystar C. G. ", "Hystar HM-75" and "Hystar TPF", all of which being available from Lonza, Inc., Fairlawn, N. J. Sorbitol would also be suitable.

The emollient should be present in the instant teat dip concentrates in an amount of about 1 to 40%, and preferably 2 to 6% by weight based on the total weight of the concentrate.

A film-forming ingredient is also required in the formulations of the present invention. Several were tried, including xanthan gum, carboxymethylcellulose, poly(vinyl alcohol), hydroxyethyl cellulose and poly(N-vinylpyrrolidone) (PVP). Surprisingly, only PVP made a stable, homogeneous solution with the "Tego 51B" germicide. The film-forming ingredient is generally employed in an amount of about 0.5 to 8% by weight based on the total weight of the teat dip concentrate. At the lower end of the above range, higher molecular weight film-forming ingredients are preferably used to give sufficient adherence of the diluted formulations to the teats.

A dye is desirably included in the teat dip formulations of the invention. Color on the teat tells farmers that they did indeed dip a particular cow. To preclude any problems with possible contamination of milk, it is preferred that only FDC Certified (food grade) dyes be used. There are 7 FDC dyes available which are generally recognized as safe, and since one of these, FDC Red #3, is now under suspicion of being a carcinogen, only 6 dyes are now considered suitable. FDC Yellow #5 is too light in color to show up well on the teats, and, therefore, it is less suitable. FDC Blue #2 is unstable in the presence of light and, therefore, is less desirable. The remaining colors are FDC Red #4, FDC Yellow #6, FDC Green #3 and FDC Blue #1. All of these colors were evaluated for inclusion in the dip. All of the colors had some slight adverse effect on the bacterial kill-rate of the dip. FDC Blue #1, however, had the least effect (See Example 6 below), and it is presently preferred. Also it is contemplated that certain D and C colors may be suitable for inclusion in the dip.

Many germicidal agents have high foaming characteristics. The germicides present in "Tego 51" and "Tego 51B" may result in foaming, and, for that reason, it is preferred to use an antifoaming agent in the formulations of the present invention. Suitable antifoaming agents are the polymers of dimethylsiloxane which are available from Dow Corning Company, an example of such being "Antifoam C". An antifoaming agent, when employed, will generally be employed in an amount of about 0.05 to 0.5% by weight based on the total weight of the teat dip concentrate.

Some known teat dips include ethylenediaminetetraacetic acid which can act as a chelating agent to remove metal ions from hard water. It has been found that ethylenediaminetetraacetic acid reduces stability and bactericidal effect of the teat dips of the invention, and, for that reason, it is preferred that the teat dips of the present invention be free of ethylenediaminetetraacetic acid.

In practice, the teat dip formulation which is prepared from the teat dip concentrate and used to dip cow teats contains at least about 90% water and preferably at least about 95% water by weight based on the total weight of the diluted formulation. The teat dip formulation should contain a germicidally effective amount of germicide selected from the group consisting of 3-(n-dodecylamino)-propylamine and 2-[2-(n-dodecylamino)ethylamino]-ethylamine, either as the free bases or acid-addition salts. It is understood that the teat dip may comprise both 3-(n-dodecylamino)-propylamine and 2-[2-(n-dodecylamino)-ethylamino]ethylamine (and/or pharmaceutically acceptable acid-addition salts of one or both of the foregoing) in amounts that together amount to a germicidally effective amount. By "germicidally effective amount" as used in the instant specification and claims is meant an amount of germicide that will provide at least about a 4 log reduction of bacterial growth when the method of Example 6 is followed and the exposure time of the inoculum to the dip is two minutes and no organic load is employed. Preferably, the teat dip will comprise both 3-(n-dodecylamino)propylamine and 2-[2-(n-dodecylamino)ethylamino]ethylamine, (or the acid-addition salts of either or both) in amounts by weight at about 0.025 to 0.25% and 0.005 to 0.10%, respectively, both based on the total weight of the teat dip formulation.

The following examples are provided to illustrate the invention, but are not intended to be limiting thereof.

EXAMPLE 1

To 700 lb. of stirred deionized water was added 1.25 lb. of the poly(dimethylsiloxane) formulation commercially available as "Antifoam C" from Dow-Corning Company, Midland, Mich. After 5 minutes of stirring, the solution was heated to 135= to 145° F. During the heating period, 8.34 lb. of poly(N-vinylpyrrolidone) of molecular weight 30,000 (commercially available under the trade designation "PVP K-30" from GAF Chemical Company, New York, NY) was added slowly, followed by slow addition of 33.34 lb. of a methyl glucose dioleate derivative of polyethylene glycol containing about 120 units of ethylene glycol per molecule (commercially available under the trade designation "Glucamate DOE 120" from Amerchol Chemical Company, Edison, NJ). Mixing was continued for 15 to 30 minutes until a solution was obtained. To this solution was added 100.08 lb. of "Tego 51B" obtained from Th. Goldschmidt Co., Essen, West Germany. Heating and mixing were continued at 135° to 145° C. for 15 minutes. To this solution was added 1.25 lb. of FDC Blue #1 (available from Warner-Jenkinson Company, St. Louis, MO), and mixing was continued for 30 minutes. The solution was then allowed to cool to ambient temperature to provide a stable, foam-free concentrate.

The amounts of each ingredient present in the final formulation were:

| | |
|---|---|
| "Tego 51B" | 12.00% |
| "Glucamate DOE 120" | 4.00% |
| "PVP K-30" | 1.00% |
| FDC Blue No. 1 | 0.15% |
| "Antifoam C" | 0.15% |
| Deionized Water | 82.70% |

EXAMPLE 2

The formulation of Example 1 was diluted with seven volumes of water to provide a solution containing 1.5% by weight of the "Tego 51B". A field trial was run on 120 dairy cows, using National Mastitis Council Protocol B.

Briefly, the National Mastitis Council Protocol B requires that each of the four teats of a cow first be dipped for ⅓ of its length in an inoculum of a given bacterium and then be drained for 5 seconds. Two teats are then dipped full length in the teat dip (over the bacteria treated teats), and the remaining two teats are maintained as untreated controls and are not dipped in the teat dip. This procedure is carried out twice a day (after each milking). Three times per week, milk is taken from each teat, a sample is plated out on suitable growth media and evaluated for bacterial growth.

The cows treated with the diluted dip of this example showed 81.2% less mastitis caused by *Staphylococcus aureus* and 67.5% less mastitis caused by *Streptococcus agalactiae* than the untreated controls. This shows that the teat dip is effective according to this nationally recognized protocol.

EXAMPLE 3

A teat dip concentrate formulation was prepared using the method of Example 1 except the amount of "Tego 51B" used was reduced by 50% and the amount of water correspondingly increased.

The amounts of each ingredient in the final formulation were:

| | |
|---|---|
| "Tego 51B" | 6.00% |
| "Glucamate DOE 120" | 4.00% |
| "PVP K-30" | 1.00% |
| FDC Blue No. 1 | 0.15% |
| "Antifoam C" | 0.15% |
| Deionized water | 88.70% |

EXAMPLE 4

The formulation of Example 3 was diluted with seven volumes of water to provide a solution containing 0.75% by weight of the "Tego 51B". A field trial was run as described in Example 2, this time on 40 dairy cows. The cows treated with the dip of Example 3 showed 52.4% less mastitis caused by *Staphylococcus aureus* but no reduction of mastitis caused by *Streptococcus agalactiae* compared to the untreated controls. This was considered a successful reduction of mastitis caused by Staphylococcus organisms.

EXAMPLE 5

The teat dip concentrate formulation of Example 1 (i.e., the formulation containing 12.00% of the "Tego 51B") was applied to all of the teats of four cows in a field trial using normal procedures (i.e., applied twice a day, after each milking) and permitted to dry. It was observed that none of the cows showed irritation of their teats after 21 days since there was no scabbing, chapping or redness.

EXAMPLE 6

Teat dip formulations were prepared according to the procedure of Example 1 using the several different dyes indicated in Table I below. The bacterial kill rate of these formulations diluted with seven parts of water was measured versus two organisms, *Staphylococcus aureus* and *Escherichia coli* using two different exposure times and with and without an organic load (i.e., 10% milk added to the formulations). The test was run by i) adding a 0.1 ml inoculum containing about $10^8$ bacteria per ml to 20 ml of the dip formulation, ii) withdrawing a 0.1 ml aliquot from said formulation and placing it on an agar plate, and iii) incubating the agar plate for 48 hours. The results were compared to untreated controls. The results are shown in Table I. The temperature of the test was 30° C., and the kill rates are shown as reductions of the total number of bacteria present on a log scale.

TABLE I

| Dye | NO ORGANIC LOAD | | 10% ORGANIC LOAD | |
|---|---|---|---|---|
| | EXPOSURE TIME | | | |
| | 2 Min. | 10 Min. | 2 Min. | 10 Min. |
| FDC Blue #1 | | | | |
| Staph. aureus | ≧6.15 | ≧6.15 | 2.30 | 5.01 |
| E. coli | ≧5.90 | ≧5.90 | 4.33 | ≧5.90 |
| FDC Green #3 | | | | |
| Staph. aureus | 3.79 | 5.01 | 2.85 | 5.53 |
| E. coli | ≧5.90 | ≧5.90 | 4.80 | ≧5.90 |
| FDC Red #4 | | | | |
| Staph. aureus | ≧6.15 | ≧6.15 | 1.99 | 4.35 |
| E. coli | ≧5.90 | ≧5.90 | 2.04 | ≧5.90 |
| FDC Yellow #6 | | | | |
| Staph. aureus | ≧6.15 | ≧6.15 | TNTC* | 3.85 |
| E. coli | ≧5.90 | ≧5.90 | 3.06 | ≧5.90 |

*TNTC = too numerous to count

What is claimed is:

1. A germicidal animal teat dip concentrate comprising, as a substantially stable homogeneous mixture, a germicide selected from the group consisting of 3-(n-dodecylamino)propylamine, a pharmaceutically acceptable acid-addition salt of 3-(n-dodecylamino)-propylamine, 2-[2-(n-dodecylamino)ethylamino]ethylamine, and a pharmaceutically acceptable acid-addition salt of 2-[2-(n-dodecylamino)ethylamino]ethylamine; as an emollient a polyethylene glycol methyl glucoside; a film-forming ingredient; and water, wherein the total amount of all germicide or germicides present in said concentrate is about 0.25 to 2.5 percent based on the total weight of said teat dip concentrate.

2. A teat dip concentrate according to claim 1, further comprising N-[3-(n-dodecylamino)propyl]glycine or a pharmaceutically acceptable acid-addition salt thereof.

3. A teat dip concentrate according to claim 1, wherein said dip concentrate comprises 3-(n-dodecylamino)propylamine in an amount of about 0.2 to 1.8 percent based on the total weight of said teat dip concentrate, and 2-[2-(n-dodecylamino)ethylamino]ethylamine or the hydrochloride salt thereof in an amount of about 0.05 to 0.7 percent based on the total weight of said teat dip concentrate.

4. A teat dip concentrate according to claim 1, wherein a dye is included.

5. A teat dip concentrate according to claim 1, wherein an antifoaming agent is included.

6. A teat dip concentrate according to claim 4, wherein an antifoaming agent is included.

7. A germicidal, substantially nonirritating animal teat dip prepared from a concentrate by the addition of water and comprising, as a substantially stable homogeneous mixture, a germicidally effective amount of a germicide selected from the group consisting of 3-(n-dodecylamino)propylamine, a pharmaceutically acceptable acid-addition salt of 3-(n-dodecylamino)propylamine, 2-[2-(n-dodecylamino)ethylamino]ethylamine, and a pharmaceutically acceptable acid-addition salt of 2-[2-(n-dodecylamino)ethylamino]ethylamine; as an emollient a polyethylene glycol methyl glucoside; a film-forming ingredient; and water, said water being present in an amount of at least about 90% by weight based on the total weight of said teat dip, wherein the total amount of all germicide or germicides present in said concentrate from which said teat dip is prepared is about 0.25 to 2.5 percent based on the total weight of said teat dip concentrate.

8. A teat dip according to claim 7, further comprising N-[3-(n-dodecylamino)propyl]glycine or a pharmaceutically acceptable acid-addition salt thereof.

9. A teat dip according to claim 7, wherein said teat dip comprises 3-(n-dodecylamino)propylamine or the hydrochloride salt thereof in an amount of about 0.025 to 0.25 percent based on the total weight of said teat dip; and 2-[2-(n-dodecylamino)ethylamino]ethylamine or the hydrochloride salt thereof in an amount of about 0.005 to 0.10 percent based on the total weight of said teat dip.

10. A teat dip according to claim 7, wherein a dye is included.

11. A teat dip according to claim 7, wherein an antifoaming agent is included.

12. A teat dip according to claim 10, wherein an antifoaming agent is included.

13. A method for controlling bovine mastitis comprising immersing the teats of a cow in a substantially nonirritating teat dip prepared from a concentrate by the addition of water and comprising, as a substantially stable homogeneous mixture, a germicidally effective amount of a germicide selected from the group consisting of 3-(n-dodecylamino)propylamine, a pharmaceutically acceptable acid-addition salt of 3-(n-dodecylamino)propylamine, 2-[2-(n-dodecylamino)ethylamino]ethylamine, and a pharmaceutically acceptable acid-addition salt of 2-[2-(n-dodecylamino)ethylamino]ethylamine; as an emollient a polyethylene glycol methyl glucoside a film-forming ingredient; and water, wherein the total amount of all germicide or germicides present in said concentrate from which said teat dip is prepared is about 0.25 to 2.5 percent based on the total weight of said teat dip concentrate.

14. A method according to claim 13, wherein said teat dip further comprises N-[3-(n-dodecylamino)propyl]glycine or a pharmaceutically acceptable acid-addition salt thereof.

15. A method according to claim 13, wherein said teat dip further includes a dye.

16. A method according to claim 13, wherein said teat dip further includes an antifoaming agent.

17. A method according to claim 16, wherein said teat dip further includes a dye.

18. A method according to claim 13, wherein said teat dip comprises 3-(n-dodecylamino)propylamine or the hydrochloride salt thereof in an amount of about 0.025 to 0.25 percent based on the total weight of said teat dip, and 2-[2-(n-dodecylamino)ethylamino]ethylamine or the hydrochloride salt thereof in an amount of about 0.005 to 0.10 percent based on the total weight of said teat dip.

19. A teat dip concentrate according to claim 1, wherein said dip is substantially free of ethylenediaminetetraacetic acid.

* * * * *